(12) United States Patent
Ivancev et al.

(10) Patent No.: US 6,773,457 B2
(45) Date of Patent: Aug. 10, 2004

(54) AORTIC GRAFT DEVICE

(75) Inventors: Krasnodar Ivancev, Lund (SE); Bansi Lal Koul, Lund (SE)

(73) Assignees: William Cook Europe ApS, Bjaeverskov (DK); Cook Incorporated, Bloomington, IN (US)

( * ) Notice: Subject to any disclaimer, the term of this patent is extended or adjusted under 35 U.S.C. 154(b) by 105 days.

(21) Appl. No.: 10/104,835

(22) Filed: Mar. 22, 2002

(65) Prior Publication Data

US 2002/0156522 A1 Oct. 24, 2002

(30) Foreign Application Priority Data

Mar. 27, 2001 (EP) .............................................. 01610036

(51) Int. Cl.[7] .................................................. A61F 2/06
(52) U.S. Cl. ..................................... 623/1.28; 623/1.13
(58) Field of Search ............................. 623/1.13, 1.24, 623/1.28, 1.32, 1.34, 1.36, 1.49

(56) References Cited

U.S. PATENT DOCUMENTS

| | | |
|---|---|---|
| 5,984,955 A | 11/1999 | Wisselink |
| 6,016,810 A | 1/2000 | Ravenscroft |
| 6,036,723 A * | 3/2000 | Anidjar et al. |
| 6,099,548 A | 8/2000 | Taheri |
| 6,203,735 B1 * | 3/2001 | Edwin et al. |
| 6,221,102 B1 * | 4/2001 | Baker et al. |

FOREIGN PATENT DOCUMENTS

| | | |
|---|---|---|
| EP | 0955019 A2 * | 11/1999 |
| WO | 9833638 | 8/1998 |
| WO | 9911198 | 3/1999 |

OTHER PUBLICATIONS

Stented Elephant Trunk Procedure For An Extensive Aneurysm Involving Distal Aortic Arch and Descending Aorta; Yukio Suto, MD, et al.; The Journal of Thoracic and Cardiovascular Surgery, vol. 112, No. 5, pp. 1389 and 1390.
Less Invasive Combined Surgical And Endovascular Stent--Graft Treatment For Descending Thoracic Aortic Aneurysms: Surgical Technical Aspects; Bansi Koul, Krassi Ivancev; Combined Open Thoracic Endovascular Techniques For Thoracic.

* cited by examiner

Primary Examiner—David O. Reip
(74) Attorney, Agent, or Firm—Richard J. Godlewski

(57) ABSTRACT

An aorta graft device comprising a primary graft part having a proximal end and a first connecting portion at a distal opening, wherein the primary graft part has an anchoring area positioned between an ascending portion extending to said proximal end and a descending portion extending to said distal opening. Furthermore, the ascending portion is corrugated, and the descending portion is at least partially non-corrugated.

18 Claims, 5 Drawing Sheets

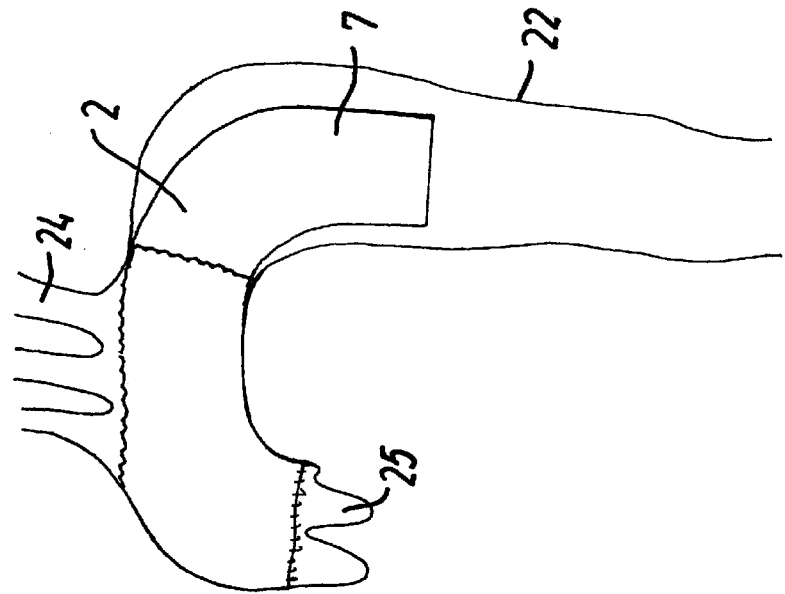
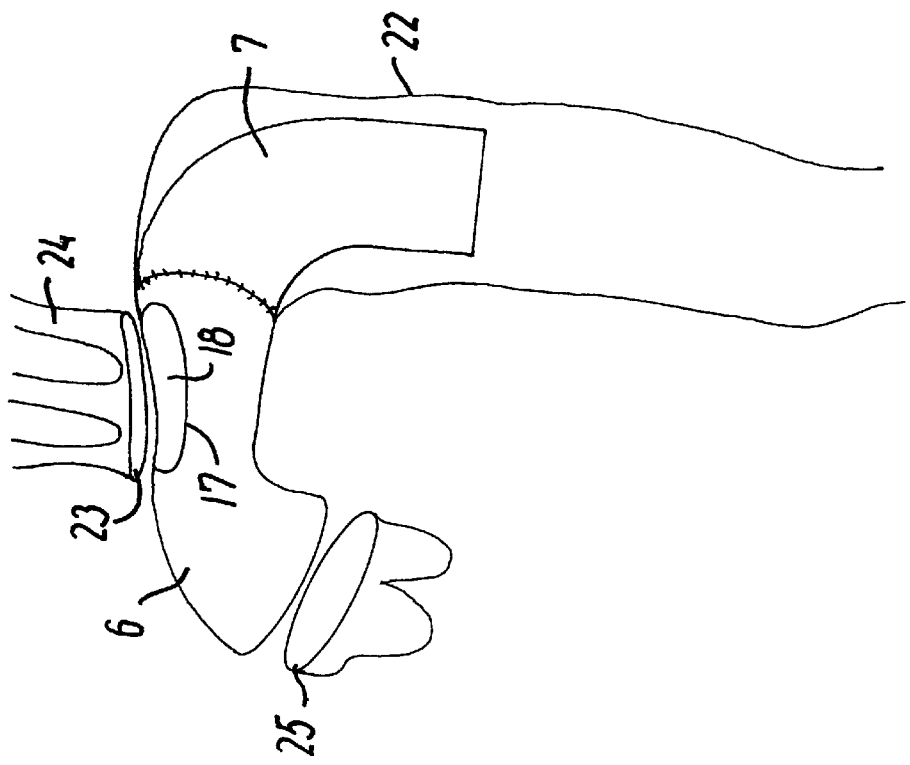

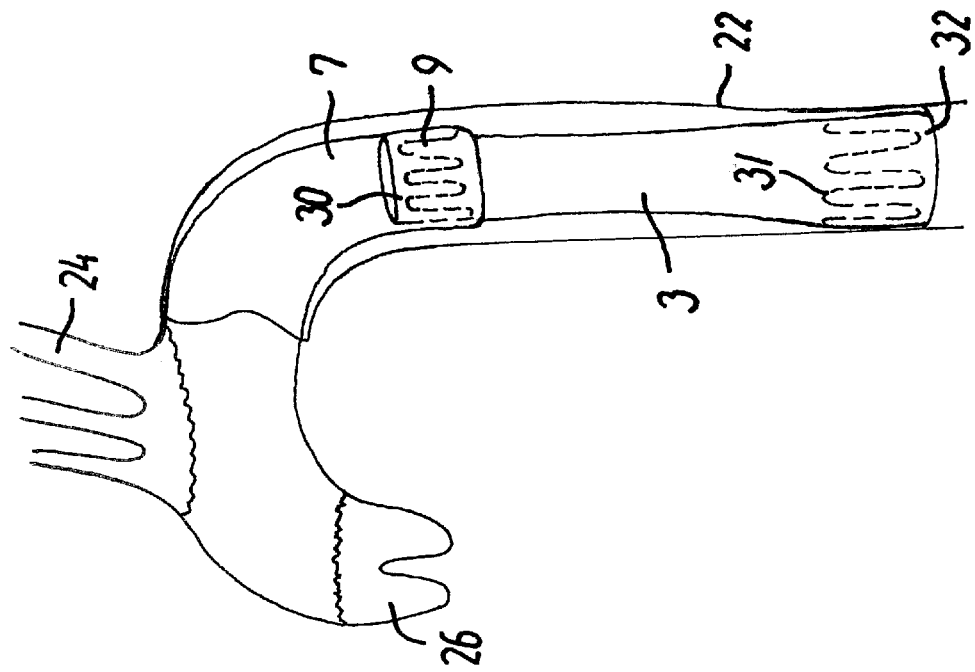
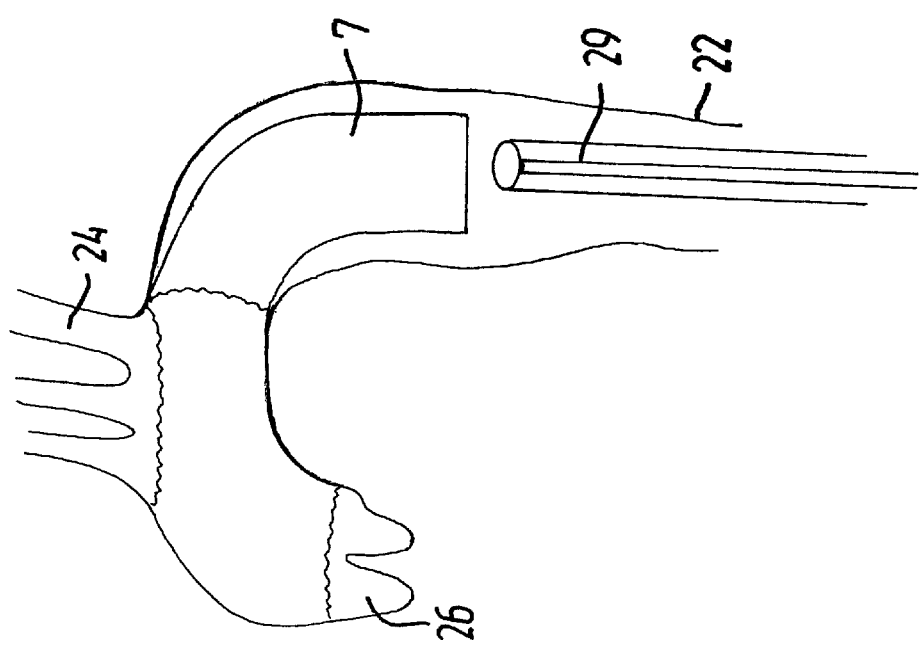

US 6,773,457 B2

AORTIC GRAFT DEVICE

CROSS-REFERENCE TO RELATED APPLICATIONS

This application claims priority of European Patent Application No. 01610036.4 filed Mar. 27, 2001.

TECHNICAL FIELD

The present invention relates to a medical device and, in particular, to an aorta graft device.

BACKGROUND OF THE INVENTION

An aorta graft is an endovascular prosthesis for placement in aorta in a weakened area, such as at an aneurysm of the abdominal aorta. An aortic aneurysm is an abnormal dilation or enlargement of the arterial wall of the aorta. If the aneurysm is not treated, it can rupture and abruptly cause a fatal blood loss out of aorta into the abdominal or thoracic cavity of patient.

The aorta graft is normally made of a tube of pliable material provided with a stent for anchoring the graft in its intended position within the blood vessel by exerting an outwardly directed radial pressure against the surrounding aortic wall. This requires in the area of the stent a relatively healthy aortic wall that can withstand the radial pressure for years. Patients diagnosed with aortic aneurysms are often in poor health due to other illnesses which increase the risk of complications associated with an operation. Most prior art aorta grafts are for the repair of abdominal aortic aneurysms (AAA) involving the pararenal and infrarenal aorta. Examples of such grafts are described in U.S. Pat. Nos. 5,984,955 and 6,016,810. Many of these grafts are bifurcated and extend into the iliac arteries. Aortic grafts of these types can typically be placed using transluminal, minimally invasive procedures where the graft is percutaneously introduced via a femoral puncture site, and the entire procedure can be performed using local anaesthesia.

With respect to aortic grafts for the repair of thoracoabdominal aortic aneurysms (aneurysms in the descending thoracic aorta) and thoracic aortic aneurysms (aneurysms in the ascending thoracic aorta including the aortic arch) only a few proposals for minimally invasive procedures have been made.

U.S. Pat. No. 6,099,548 proposes to advance the graft into the ascending thoracic aorta and to lock it to the aortic wall by expanding a stent in the proximal end of the graft. However, adjacent the heart the flow rate of blood through aorta is so high that the risk of dislocation of the proximal stent is considerable.

In a particularly lethal kind of aortic aneurysms the aortic wall is dissected to form a bogus lumen that establishes a parallel flow path for blood. The only method of repair is open surgery. In a so-called elephant trunk procedure a stented distal end of a secondary graft part is fixed in the descending aorta, and the proximal end of the secondary graft part is sutured to a primary graft part that is placed in the ascending aorta and anastomosed to the branch arteries carotis communis, subclavia and truncus brachiocephalicus.

During the operation the patient is subjected to cardiac arrest and systemic circulatory arrest, and although the patient has been cooled to a very low body temperature, such as 16° C., and selective cerebral perfusion is performed, the duration of the operation is a critical factor.

Dissections of type A where the aortic wall dissection is initiated in the ascending aorta pose a particular problem. With the prior art techniques the mortality is 75% within 24 hours of initiation of the condition and 90% within one week. The surgeon thus has extremely short time to prepare and perform the surgery.

SUMMARY OF THE INVENTION

A purpose of the present invention is to improve the efficiency of the surgical repair of implanting the aortic graft device.

With a view to this the aortic graft device according to the invention is characterized in that the primary graft part has an anchoring area positioned between an ascending portion extending to said proximal end and a descending portion extending to said distal opening, that the ascending portion is corrugated, and that the descending portion is at least partially non-corrugated.

The positioning and anchoring of the primary graft part can begin immediately after cardiac arrest has been obtained. The corrugations on the ascending portion of the graft facilitates setting of the ascending portion in a curvature following the path of the ascending aorta in the particular patient. This saves some time. A further major time saving is obtained in that the primary graft part is the first one to be positioned in the patient. After anchoring the primary graft part to the aortic wall, the ascending portion of the graft can be located in the ascending aorta and the descending portion of the primary graft part can be left hanging loose in the descending aorta. Time consuming suturing of the secondary graft part to the primary graft part is avoided which markedly reduces the duration of the critical part of the operation in which cardiac arrest and systemic circulatory arrest are required.

The non-corrugated area on the descending portion makes it possible to connect the descending portion of the graft to a secondary graft part or to the aortic wall at a subsequent operation. When the surgeon has performed the anchoring of the primary graft part he is aware of the time consumed and he can decide to insert a secondary graft part right away if time allows this, or to postpone placement of a secondary graft part or an alternative connection of the distal end of the primary graft part to the aortic wall to another operation. The surgeon also fixes the proximal end of the primary graft part to the desired site of the aortic wall in the ascending aorta.

The anchoring area positioned between the ascending and the descending portions of the primary graft part make it possible for the graft to be fixed to a portion of the aortic wall in vicinity of the three branch arteries on the aortic arch. The anchoring can be made to the distal side of the arteria subclavia at least at the upper portion of the aortic arch and possibly in an annular pattern following the aortic wall.

In an illustrative embodiment, the descending portion of the primary graft part is non-corrugated at least at said first connecting means, and preferably along its full length from said anchoring area to said distal opening. The non-corrugated area makes it easier to obtain a blood tight connection between the primary graft part and the tubular member connected to it.

The descending portion of the primary graft part is provided with at least one stent, and preferably provided with at least two stents, which are located near the anchoring area and at the distal opening, respectively. The stent resiliently acts on the descending portion to keep it open and non-kinking.

In a further embodiment the descending portion of the primary graft has a distal end area which is uncorrugated and unstented and has a length of at least 20 mm. The distal end area can be utilized to couple the primary graft to either a secondary graft or to the aortic wall. It is possible to perform suturing in the distal end area, but it is likewise possible to use the smooth surface character in the distal end area to obtain a pressure-tight sealing between the primary graft and the secondary graft.

The descending portion of the primary graft part is preferably supported by a stent at least along the majority of its length. By stenting, the descending portion is kept fully open, also when it is subjected to compressing or kinking actions on the exterior of the descending portion which is hanging freely floating in the aortic vessel downstream of the anchoring area. This is particularly useful when a secondary graft part is to be connected to the primary graft part at separate surgery.

In order to facilitate handling and placement of the primary graft at least the ascending portion of the primary graft part is precurved. The precurved shape reduces the size of bending forces required to keep the ascending portion in position during suturing of the anchoring area and thus minimizes the time spent on correcting the location of the primary graft part during suturing.

In a preferred embodiment, a wedge-shaped area of graft side wall in the ascending portion has been removed and the exposed opposite rim areas have been joined to each other. The removal of the wedge-shaped area results in a distinct or sharp bend in the graft part at the place of the removed material and allows on the one hand manufacturing of the graft part as a straight tubular part with uniform properties and on the other hand the more sharp bend can be obtained in a comparatively easy manner.

It is preferred that the ascending portion has a length in the range of from 11 to 17 cm, that said descending portion has a stented length in the range of from 5 to 10 cm, and that said distal end area has a length in the range of from 2 to 3 cm. These features make the primary graft part quite flexible in the rather long corrugated ascending portion and well suited to accept different kinds of fixation modes in the descending portion, such as fixation to a secondary graft part which is fixed to the natural aortic wall, or fixation of the descending portion directly to the natural aortic wall.

When a patient is suffering from a dissection of type A, the development of the dissection and the paths it follows can be somewhat unpredictable, and in order to be more certain that every part of the dissection is blocked at a particular location in the aorta, the anchoring area can comprise an annular area encircling the primary graft part. This allows for a fixation of the graft to the aortic wall along a full circumference of the wall.

It is preferred that said annular area is uncorrugated and unstented and has a length of at least 10 mm. The surgeon can quickly fix this annular anchoring area to the aortic wall because the area is free from pre-manufactured corrugations and stents and has a length that provides easy access to a contact point between graft and wall when the suture is to be applied.

The anchoring area can in an embodiment include a lateral area which extends away from the annular area in direction of the ascending portion. This lateral area can be positioned next to the three branch arteries and quickly be fixed to the aortic wall.

In a further development of the latter embodiment the lateral area is carrying a marking, such as a coloring distinct from the remainder of the primary graft part. The coloring makes it very easy and thus quick for the surgeon to position the primary graft part with the lateral area facing correctly in the cranial direction.

In yet a further development the lateral area includes a lateral opening so that the surgeon does not spend additional time for providing communication between the aorta vascular space inside the graft and the aortic branch arteries.

The primary graft part can be supplied in or be set into a mounting state where the ascending portion has been everted into said descending portion to present said annular anchoring area as a rim area to be sutured to the aortic wall.

A dissection of type A can extend into the area of the heart valve and depending on the actual circumstances, such as whether a coronary artery is involved in the dissection, it can be insufficient to repair only the aorta. If additional surgery is required on the heart valve, the graft device preferably also includes an end portion with a heart valve.

When the graft device includes a heart valve it is preferred that the primary graft part has a proximal opening, and that the end portion with the heart valve is a separate part to be fixed to said primary graft part at said proximal opening. This division of the graft device allows the surgeon to split the surgery into separate rounds where the time consuming fixation of the end portion to the heart and coronary arteries can be performed while the circulatory system is functioning by a cardio-pulmonary bypass and appropriate cannulations. Then, in a second round, the primary graft part can be applied after establishing systemic circulatory arrest, but the duration of circulatory arrest is considerably shortened by performing a large part of the surgery required during said first round.

As mentioned above, the descending portion of the primary graft part can be connected to the aortic wall in different manners. In one embodiment, the graft device includes a secondary graft part with a second connecting means that by engagement with said first connecting means connects said secondary graft part to said primary graft part. Use of the secondary graft part can often be a preferred alternative to suturing of the descending portion to the aortic wall. The second connecting means makes possible a quick establishment of the interconnection between the parts.

This embodiment can be further developed so that the engagement involves geometrically interlocking parts on said first and second connecting means, respectively, preferably so that the engagement is enhanced when said secondary graft part is pulled in the distal direction. The geometrical locking of the two parts can provide better long term durability of the graft device which continuously is subjected to the pressure pulses produced by the heart beats.

BRIEF DESCRIPTION OF THE DRAWING

Embodiments of the present invention are explained in more detail in the following with reference to the highly schematical drawings, on which FIGS. 3–8 illustrate an example of deployment of the device in FIG. 1, and FIG. 9 illustrate another embodiment of the device according to the present invention.

DETAILED DESCRIPTION

Figure 1:
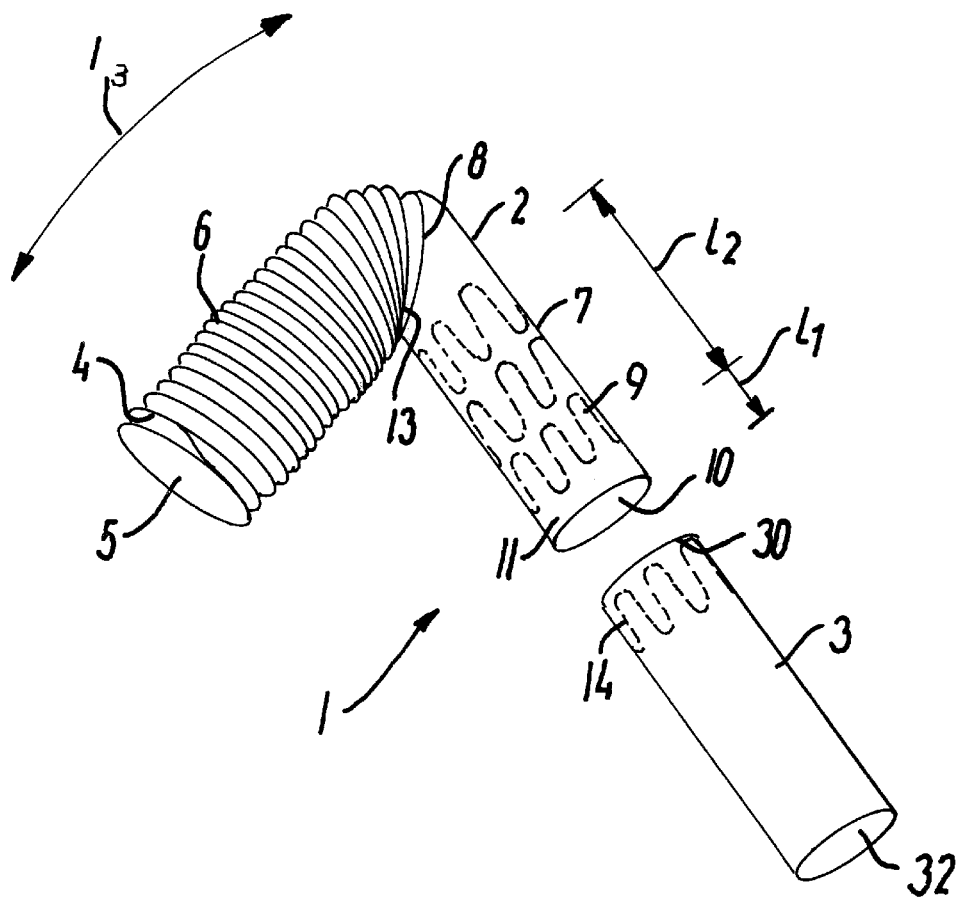
FIGS. 1 and 2 depict two embodiments of an aorta graft device according to the present invention.

An aorta graft device illustrated in FIG. 1 is generally designated 1 and includes a primary graft part 2 and an optional secondary graft part 3. The primary graft part 2 is tubular and has a proximal end 4 with a proximal opening 5. In the present context proximal is used for something located closer to the heart or to the side of the heart whereas distal is used for something located more distant from the heart.

The primary and secondary graft parts are tubular and can be made of a pliable material, such as expanded polytetrafluoroethylene (PTFE), woven polyester or another biocompatible material of long term stability in the vascular system. Graft materials are well known in the art and the material can also include the biodegradeable strands as part of the material.

The primary graft part has an ascending portion 6 and a descending portion 7. An anchoring area 8 is positioned in between the two portions 6, 7. The ascending portion 6 is at least partially corrugated (crimped) or folded in order to promote setting of the ascending portion in a curved shape and flexibility of the graft in use.

The descending portion 7 is at least partially non-corrugated, and it can be non-corrugated along its complete surface. It can of course alternatively be corrugated along only part of its circumference and/or its length. The descending portion 7 can be unstented along its entire length, but preferrably it is at least partially stented by a stent 9 located at a distal opening 10. Stent 9 is of well known construction. It can e.g. be a so-called Gianturco Z-stent or another stent of expandable or self-expandable type which typically is of nitinol, stainless steel or another biocompatible material. Stent 9 is typically placed inside the tubular graft material, but can alternatively be placed on the outside of the tubular material which is then fastened to the stent struts, or the stent can be integrated into the graft material.

Figure 9:
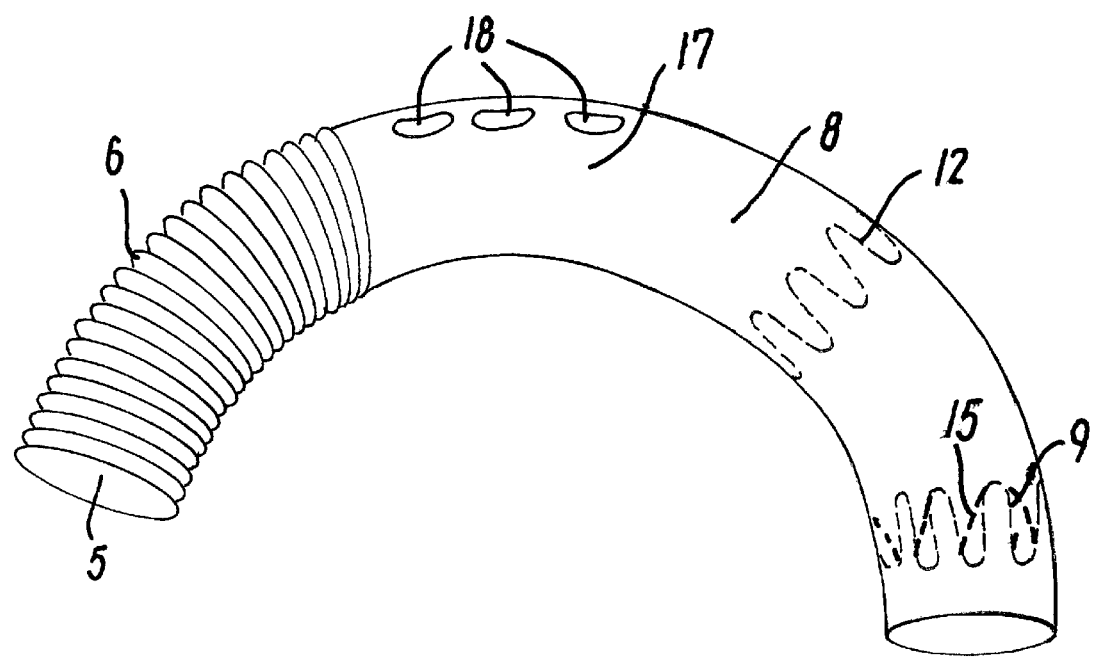

Next to distal opening 10 the descending portion has a distal end area 11 which is unstented and can have a length 11 in the range from 3 mm to 40 mm, preferably from 20 mm to 30 mm. Stent 9 can extend continuously from distal end area 11 to the anchoring area 8. As depicted in FIG. 9 there can also be used two (or more) separate stents 9, 12 located at a distance from each other. The stent or stents keep the anchoring area in a stretched tubular shape ready for suturing and keep the distal opening in an open state that is accessible from the distal part of the aorta. In FIG. 1 the stented length 12 of the descending portion is in the range of 5 cm to 10 cm. The ascending portion has a length 13 in the range from 11 cm to 17 cm. The diameter of the graft device is in the range from 22 mm to 38 mm, preferably from 30 mm to 34 mm, such as about 32 mm. The tubular graft material has typically an even diameter along its length when it is manufactured, and some variations in diameter can result from the crimping of the ascending portion. However, it is also possible to make the graft of two separate tubular parts of different diameter if the ascending portion is to be of a diameter different from the descending portion of the graft device.

At the lower (concave) side of the tubular graft a wedge-shaped area of the material has been cut away and the rim areas 13 have been joined, such as by suturing.

The secondary graft part 3 has a connecting means 14 depicted as a stent in its proximal end. When the secondary graft part has been inserted through distal opening 10 into descending portion 7 and has been expanded, whether by self-expansion or balloon expansion, the connecting means 14 engages with stent 9 acting as a first connecting means on the primary part. The engagement can be of the frictional type produced by the radially outward pressure from stent 14 on the inside of the descending portion, but it is preferred that the mutual engagement involves geometrically interlocking parts, such as hooks 15 on stent 9 (FIG. 9). The hooks extend obliquely in the proximal direction. The hooks penetrate the graft material of graft part 3 and engage with the struts of stent 14 when the graft part 3 is pulled slightly in the distal direction.

In the following description of embodiments the same reference numerals are used for details of the same type.

Figure 2:
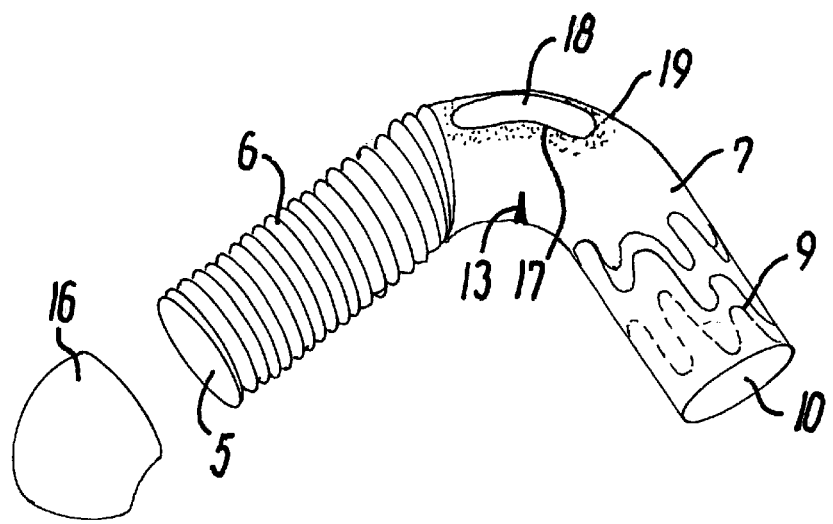

In FIG. 2 the graft device also includes an end portion 16 with a heart valve. The stent 9 runs in a spiral pattern from one end to the other of the descending portion 7. The anchoring area includes a lateral area 17 extending annularly around a lateral opening 18 to be positioned at the three major branch arteries from the aortic arch. Lateral opening 18 can be part of the graft device as manufactured or it can be cut by the surgeon after he has opened the patient and ascertained the actual dimensions and locations of the proximal end opening of the branch arteries. In the latter case the lateral area can have a marking 19, such as a coloring, clearly indicating where the upwards facing lateral anchoring area is located on the graft device. This allows the surgeon to immediately position the graft device correctly and also helps to ensure that the cutting of the lateral opening or openings is only done in the unstented anchoring area. FIG. 9 illustrates an embodiment with three lateral openings 18.

With reference to FIGS. 3–8 there is in the following shortly described an example of how the aorta graft device can be deployed.

After cooling the patient down and exposing the aortic arc through a sternotomy and performing cardiopulmonary bypass or systemic circulatory arrest the ascending portion of aorta is resected, thereby exposing an proximal end opening 21 on the descending aorta 22 and a proximal end area 23 at the three major branch arteries 24 and a distal end opening 25 at the heart valve 26.

Figure 4:
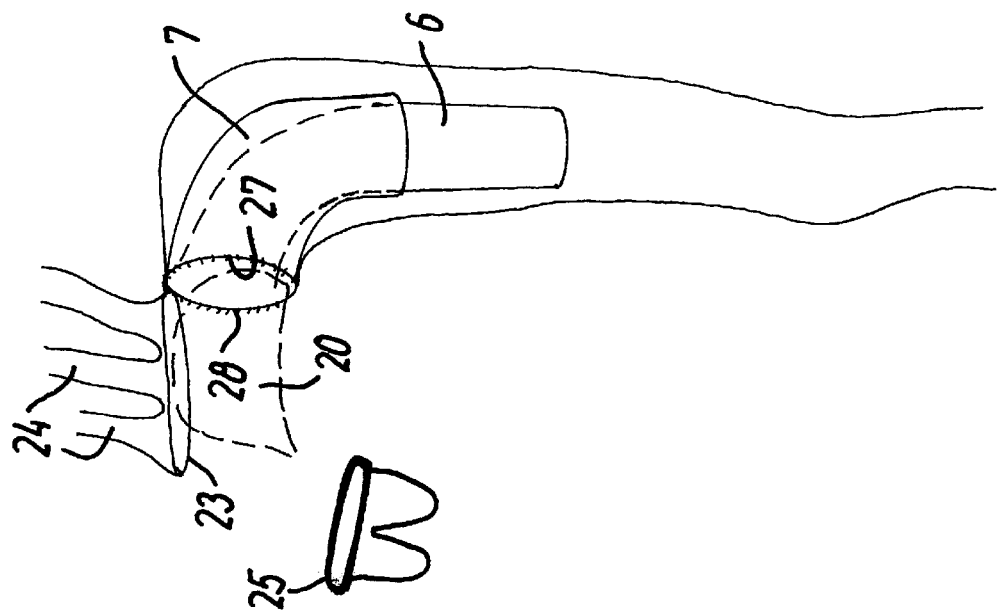
Figure 3:
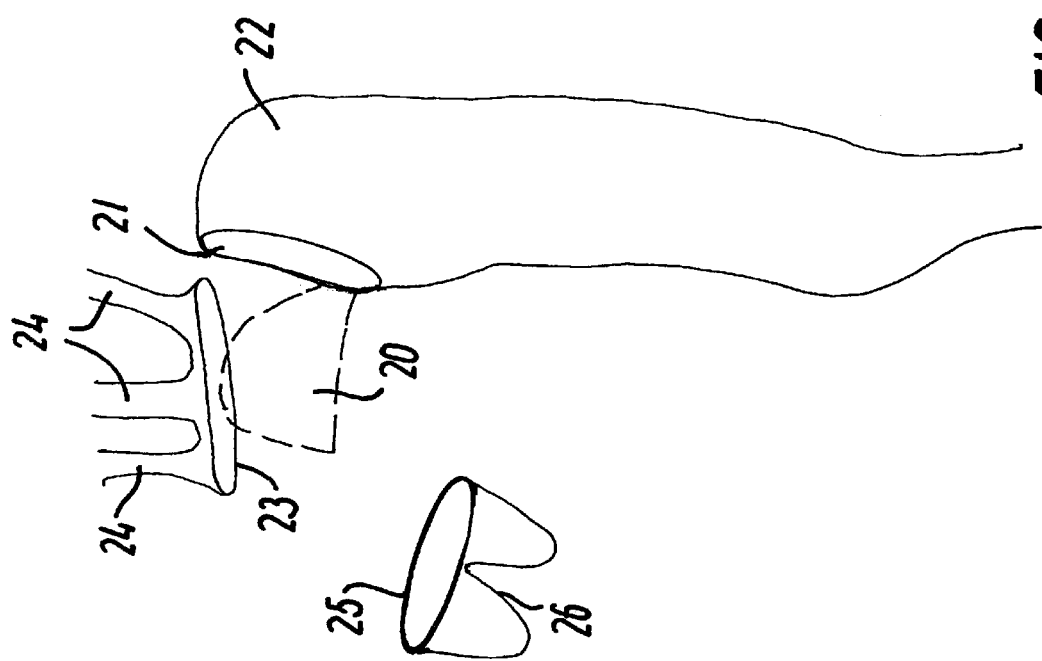

The graft device is in a mounting state with the ascending portion 6 inverted down into the descending portion 7 (FIG. 4). The graft device is inserted into the descending aorta and is placed with a rim area 27 at the end opening 21 and then the rim area 27 on the graft is fixed to the aortic wall, such as by suturing 28 or stapling.

After fixing of the graft to the aortic wall the ascending portion of the graft is inverted to the position illustrated in FIG. 5 with lateral opening 18 located at the proximal end area 23. Then this end area 23 is joined with the lateral anchoring area 17, such as by suturing or stapling. At this point in time the surgeon can decide to insert the secondary graft part through the proximal opening 5 and mount it in the ascending aorta and/or to the descending portion of the primary graft part. In many cases the decision will be to postpone the placement of the secondary graft part to a separate surgery in order to reestablish circulation as quickly as possible. Then the rim area at the proximal opening 5 is joined with the rim area at the distal end opening 25, such as by suturing or stapling.

The graft device is then in the state illustrated in FIG. 6 where the circulation can be reestablished. The descending portion is hanging loose into the aorta. Depending on the condition and desires of the patient it is then possible to proceed in alternative ways. One possibility is to open the patient from the side and secure the end area 11 to the aortic wall, such as by suturing or stapling or stenting. Another possibility is to add the secondary graft part 3 which can be done either by percutaneously introducing (e.g. femorally) and intraluminally advancing graft part 3 with a minimally invasive procedure or by performing open surgery where the patient is opened from the side and the secondary graft part is introduced after establishing suitable cannulation and bypass.

FIG. 7 illustrates the introduction of the secondary graft part 3 held in a radially reduced state in an introducer 29.

When the proximal end 30 of graft part 3 is correctly located in the descending portion 7 the proximal end 30 is released from or expanded by the introducer so that the first and second connecting means are brought into secure mutual engagement. Then a distal end 32 of the secondary graft part 3 is located at the desired site of the aorta and is fixed thereto, either by suturing or stapling or by stenting. FIG. 8 illustrates stenting with a distal most stent 31 in the distal end.

Details of the above mentioned embodiments can be combined into other embodiments within the scope of the present invention.

What is claimed is:

1. An aorta graft device comprising a primary graft part having a proximal end and a first connecting means at a distal opening, wherein the primary graft part has an anchoring area positioned between an ascending portion extending to said proximal end and a descending portion extending to said distal opening, wherein the ascending portion is corrugated, and wherein the descending portion is at least partially non-corrugated.

2. An aorta graft device according to claim 1, wherein the descending portion of the primary graft part is non-corrugated at least at said first connecting means, and preferably along its full length from said anchoring area to said distal opening.

3. An aorta graft device according to claim 1, wherein the descending portion of the primary graft part is provided with at least one stent, and preferably provided with at least two stents, which are located near the anchoring area and at the distal opening, respectively.

4. An aorta graft device according to claim 1, wherein the descending portion of the primary graft part is supported by stent at least along the majority of its length.

5. An aorta graft device according to claim 1, wherein said anchoring area comprises an annular area encircling the primary graft part.

6. An aorta graft device according to claim 1, wherein the graft device includes a secondary graft part with a second connecting means that by engagement with said first connecting means connects said secondary graft part to said primary graft part.

7. An aorta graft device comprising a primary graft part having a proximal end and a first connecting means at a distal opening, wherein the primary graft part has an anchoring area positioned between an ascending portion extending to said proximal end and a descending portion extending to said distal opening, wherein the ascending portion is corrugated, wherein the descending portion is at least partially non-corrugated, wherein the descending portion of the primary graft part is provided with at least one stent, and preferably provided with at least two stents, which are located near the anchoring area and at the distal opening, respectively, and wherein the descending portion of the primary graft has a distal end area which is uncorrugated and unstented and has a length of at least 20 mm.

8. An aorta graft device according to claim 7, wherein said ascending portion has a length in the range from 11 to 17 cm, wherein said descending portion has a stented length in the range from 5 to 10 cm, and wherein said distal end area has a length in the range from 2 to 3 cm.

9. An aorta graft device comprising a primary graft part having a proximal end and a first connecting means at a distal opening, wherein the primary graft part has an anchoring area positioned between an ascending portion extending to said proximal end and a descending portion extending to said distal opening, wherein the ascending portion is corrugated, wherein the descending portion is at least partially non-corrugated and wherein at least the ascending portion of the primary graft part is precurved.

10. An aorta graft device comprising a primary graft part having a proximal end and a first connecting means at a distal opening, wherein the primary graft part has an anchoring area positioned between an ascending portion extending to said proximal end and a descending portion extending to said distal opening, wherein the ascending portion is corrugated, wherein the descending portion is at least partially non-corrugated and wherein the ascending portion a wedge-shaped area of graft side wall has been removed and the exposed opposite rim areas joined to each other.

11. An aorta graft device comprising a primary graft part having a proximal end and a first connecting means at a distal opening, wherein the primary graft part has an anchoring area positioned between an ascending portion extending to said proximal end and a descending portion extending to said distal opening, wherein the ascending portion is corrugated, wherein the descending portion is at least partially non-corrugated and wherein said anchoring area comprises an annular area that is uncorrugated, unstented and has a length of at least 10 mm.

12. An aorta graft device comprising a primary graft part having a proximal end and a first connecting means at a distal opening, wherein the primary graft part has an anchoring area positioned between an ascending portion extending to said proximal end and a descending portion extending to said distal opening, wherein the ascending portion is corrugated, wherein the descending portion is at least partially non-corrugated, wherein said anchoring area comprises an annular area encircling the primary graft and wherein said anchoring area includes a lateral area extending away from the annular area in direction of the ascending portion.

13. An aorta graft device according to claim 12, wherein said lateral area is carrying a marking.

14. An aorta graft device according to claim 12, wherein said lateral area includes a lateral opening.

15. An aorta graft device comprising a primary graft part having a proximal end and a first connecting means at a distal opening, wherein the primary graft part has an anchoring area positioned between an ascending portion extending to said proximal end and a descending portion extending to said distal opening, wherein the ascending portion is corrugated, wherein the descending portion is at least partially non-corrugated and wherein a mounting state of said primary graft part the ascending portion has been everted into said descending portion to present said annular anchoring area as a rim area.

16. An aorta graft device comprising a primary graft part having a proximal end and a first connecting means at a distal opening, wherein the primary graft part has an anchoring area positioned between an ascending portion extending to said proximal end and a descending portion extending to said distal opening, wherein the ascending portion is corrugated, wherein the descending portion is at least partially non-corrugated and wherein the graft device includes an end portion with a heart valve.

17. An aorta graft device according to claim 16, wherein the primary graft part has a proximal opening, and wherein the end portion with the heart valve is a separate part to be fixed to said primary graft part at said proximal opening.

18. An aorta graft device comprising a primary graft part having a proximal end and a first connecting means at a distal opening, wherein the primary graft part has an anchoring area positioned between an ascending portion extending to said proximal end and a descending portion extending to said distal opening, wherein the ascending portion is corrugated, wherein the descending portion is at least partially non-corrugated and wherein the engagement involves geometrically interlocking parts on said first and second connecting means, respectively, whereby the engagement is enhanced when said secondary graft part is pulled in the distal direction.

* * * * *